(12) United States Patent
Papastathopoulos (10) Patent No.: US 10,470,930 B2
(45) Date of Patent: Nov. 12, 2019

(54) METHOD AND SYSTEM FOR ADJUSTING A LASER-BASED TREATMENT SYSTEM TO AN EYE

(71) Applicant: Carl Zeiss Meditec AG, Jena (DE)

(72) Inventor: Evangelos Papastathopoulos, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 487 days.

(21) Appl. No.: 15/025,875

(22) PCT Filed: Sep. 29, 2014

(86) PCT No.: PCT/EP2014/070733
§ 371 (c)(1),
(2) Date: Mar. 29, 2016

(87) PCT Pub. No.: WO2015/044402
PCT Pub. Date: Apr. 2, 2015

(65) Prior Publication Data
US 2016/0235584 A1    Aug. 18, 2016

(30) Foreign Application Priority Data
Sep. 30, 2013   (DE) ........................ 10 2013 219 829

(51) Int. Cl.
*A61F 9/008*    (2006.01)

(52) U.S. Cl.
CPC .... *A61F 9/008* (2013.01); *A61F 2009/00851* (2013.01); *A61F 2009/00855* (2013.01)

(58) Field of Classification Search
CPC ..................................................... A61F 9/008
USPC ......................................................... 606/4–6
See application file for complete search history.

(56) References Cited

U.S. PATENT DOCUMENTS

| 8,403,921 B2 | 3/2013 | Palankar et al. |
| 2009/0131921 A1 | 5/2009 | Kurtz et al. |
| 2009/0137993 A1 | 5/2009 | Kurtz |

(Continued)

FOREIGN PATENT DOCUMENTS

| DE | 11 2008 002 383 T5 | 6/2010 |
| WO | WO 2013/096348 A1 | 6/2013 |

OTHER PUBLICATIONS

The International Preliminary Report of PCT/EP2014/070733 dated Apr. 14, 2016 along with it's English Translation.

*Primary Examiner* — Lynsey C Eiseman
(74) *Attorney, Agent, or Firm* — Christensen, Fonder, Dardi & Herbert PLLC (57) ABSTRACT

A method for adjusting a scanning laser-treatment device to an eye, including: using a laser-treatment device for emitting treatment laser radiation, a handpiece into which the radiation is coupled and having multiple markings and an outlet end for emitting the radiation into the eye, and a laser scanner arranged between a radiation source and the outlet end; using an OCT module with a scanner to image eye structures, the handpiece and the module being movable relative to each other in a first state, and the handpiece coupling to the module to image the eye through the outlet end; imaging the markings and ascertaining a first relative position between the markings and the OCT scanner; imaging an eye structure using the module through the handpiece and outlet end, and ascertaining a second relative position; and generating signals to actuate the laser scanner based on the first and the second relative positions.

10 Claims, 5 Drawing Sheets

(56) References Cited

U.S. PATENT DOCUMENTS

2013/0102895 A1     4/2013    Gooding et al.
2013/0158531 A1     6/2013    Goldschleger et al.

METHOD AND SYSTEM FOR ADJUSTING A LASER-BASED TREATMENT SYSTEM TO AN EYE

PRIORITY CLAIM

The present application is a National Phase entry of PCT Application No. PCT/EP2014/070733, filed Sep. 29, 2014, which claims priority from German Patent Application Number 102013219829.9, filed Sep. 30, 2013, the disclosures of which are hereby incorporated by reference herein in their entirety.

FIELD OF THE INVENTION

The invention relates to a method for adjusting a scanning laser-based treatment device to an eye and a system for laser treatment with scanning laser radiation.

BACKGROUND OF THE INVENTION

Many eye diseases can be treated with laser radiation. A prominent example is cataract surgery, i.e., the exchange of the impaired eye lens for an implant. Treatment laser radiation is focused into the eye of the patient in order to produce cuts at predefined locations and to enable the impaired eye lens to be removed. The treatment laser radiation is focused into the eye and the focus position is shifted in the eye. For this, a laser scanner is provided, which scans the laser radiation over the eye, for example, to apply a pulsed laser radiation in the lens of the eye by shifting the focus position such that this lens can be comminuted and removed.

For the action of the laser radiation, in particular pulsed laser radiation, the target points for the focus position must be directed precisely to specified structures of the eye. It is therefore known to produce a three-dimensional image at least of the specified structures of the eye, in some cases even of the whole eye, by means of optical coherence tomography. A respective method and device are known from US 2013/0102895 A1. There the beam path of an OCT module is combined with the beam path of the treatment laser radiation and then supplied to the laser scanner. It is thereby achieved that the OCT imaging takes place at exactly the same location as that to which the treatment laser radiation is also focused. A systematically similar construction is known from U.S. Pat. No. 8,409,921 B1, which likewise combines the beam path of an OCT with the beam path of a treatment laser and deflects it in the eye via a common laser scanner.

In both of the named devices, a contact lens can be used in order to make a coupling-in of the radiation into the eye easier and in particular to fix the eye spatially. According to US 2013/0102895 A1, adjustment marks can be provided on the contact lens which are made to coincide with markings applied to the cornea before surgery, in order to bring the eye into the correct position with respect to the laser treatment system. The correct position of the eye can be checked with an additional camera, which generates a wide image of the contact lens and the cornea. For the adjustment process, U.S. Pat. No. 8,409,921 B1 uses a separate surgical microscope, which is used before the laser treatment system and, after suitable examination of the eye, is replaced by the laser treatment system.

US 2009/0137993 A1 likewise relates to a laser treatment system which uses treatment laser radiation to modify certain structures of the eye. Here, the treatment progress can be observed by means of an optical coherence tomograph (OCT) or a camera, and in particular the focal position of the treatment laser beam can be checked during the treatment. The OCT or the camera also images the area of the eye in which the focus is shifted. The OCT and the laser treatment device can be present as separate or as combined systems. If both systems use the same contact lens, the OCT can be used in order not only to capture selected areas of specified eye structures which are to be treated, but also to image selected areas of the contact lens. In all embodiments of US 2009/0137993, in particular in the embodiments in which separate scanners are used in each case for treatment laser radiation and OCT imaging, the OCT serves to check the position of the focus of the treatment laser radiation in the specified structures of the eye in that the OCT images precisely these specified structures during the treatment procedure.

In order to rule out misalignments of the focus of the treatment laser radiation in the eye, in the state of the art according to US 2009/0137993 A1 it is necessary to image the corresponding eye structures using optical coherence tomography simultaneously as far as possible. In time periods in which no OCT imaging takes place, the position of the focus of the treatment laser radiation with respect to the specified structures to be treated cannot be monitored. Any movements of the eye during such time periods would lead to a misalignment of the focus of the treatment laser radiation.

SUMMARY OF THE INVENTION

An object of the invention is to deliver a method for adjusting a scanning laser treatment device to an eye and a corresponding system for laser treatment, which ensure with a low outlay that the treatment laser radiation is directed exactly at specified structures of the eye.

This object is achieved according to the invention with a method for adjusting a scanning laser-based treatment device to an eye, wherein the method comprises the following steps:

a) using a laser-based treatment device which comprises
   a laser beam source for emitting treatment laser radiation,
   a handpiece into which the treatment laser radiation is coupled and which comprises at least three markings and an outlet end for emitting the treatment laser radiation into the eye,
   a controllable laser scanner which is arranged between the laser beam source and the outlet end and is rigidly connected to the adjustment structure in order to guide the treatment laser radiation over the eye in a scanning manner;

b) using an OCT module with a controllable OCT scanner in order to image structures of the eye in a scanning manner, wherein the handpiece and the OCT module are freely movable relative to each other in a first state, and the handpiece comprises a coupling point for the OCT module in order to image the eye through the outlet end;

c) imaging the markings provided on the handpiece using the OCT module and ascertaining a first relative position between the markings of the handpiece and the OCT scanner;

d) imaging a specified structure of the eye using the OCT module through the handpiece and the outlet end and ascertaining a second relative position between the specified structure and the OCT scanner, and e) generating signals in order to actuate the laser scanner on the basis of the first and the second relative position.

The object is further achieved by a system for laser treatment which comprises:

a laser treatment device which comprises
- a laser beam source for emitting treatment laser radiation,
- a handpiece into which the treatment laser radiation is coupled and which comprises at least three markings and an outlet end for emitting the treatment laser radiation into the eye,
- a controllable laser scanner which is arranged between the laser beam source and the outlet end and is rigidly connected to the adjustment structure in order to guide the treatment laser radiation over the eye in a scanning manner;

an OCT module with a controllable OCT scanner in order to image structures of the eye in a scanning manner, wherein the handpiece and the OCT module are freely movable relative to each other in a first state, and the handpiece comprises a coupling-in point for the OCT module in order to image the eye through the outlet end, and a control device, which is designed
- to actuate the OCT module to generate an image of the markings provided on the handpiece using the OCT module and to ascertain from the image of the markings a first relative position between the markings and the OCT scanner;
- to actuate the OCT module to generate an image of a specified structure of the eye through the handpiece and the outlet end and to ascertain from the image of the markings a second relative position between the specified structure and the OCT scanner, and
- to generate signals in order to actuate the laser scanner on the basis of the first and the second relative position.

The invention makes use of a handpiece, which comprises markings which are captured using the OCT module and are used as a reference for the position of the handpiece and thus of the laser scanner. Using the markings, the relative position between the OCT module and the handpiece, and thus ultimately between the OCT scanner and the laser scanner, is ascertained. Although the laser treatment device (and thus the laser scanner) and the OCT module (and thus the OCT scanner) are freely movable relative to each other, the relative position between the named elements is known through the imaging of the markings using the OCT module. If specified structures in the eye are captured using the OCT module, a second relative position has been ascertained, namely between the specified structures and the OCT scanner. Because of the known first relative position, the (third) relative position between the laser scanner and the specified structures is automatically also known. The position of the focus of the treatment laser radiation can be set with high precision with respect to the specified structures.

The approach according to the invention allows a laser treatment device and an OCT module to be used which are designed as stand-alone devices. In particular, the OCT module can be provided in a surgical microscope. The handpiece and the OCT module can be attached to stand-alone frames without the positioning having to be determined, via a frame attachment, in a manner which is demanding in terms of mechanics and signalling.

Because of the measurement principle used, the OCT module has a very large axial measurement range. Therefore, in an embodiment, it is provided to capture both the markings which are fixed with respect to the laser scanner and the structures of the eye to be captured simultaneously or essentially simultaneously without problems, in any case without a laborious shifting of an optical measuring device. This is particularly advantageous if the first state, in which the OCT module is not rigidly connected to the handpiece, is also maintained during the operation of the laser treatment system. Through repeated capture of the position of the markings and of the specified structures of the eye, first and second relative positions can be constantly ascertained. Any relative movements between the OCT module and the handpiece and/or between the handpiece and the eye are thus identified at once and can be immediately taken into account in the actuation of the laser scanner.

If it is desired to use an OCT module which is particularly low-outlay and the axial measurement range of which is smaller than the distance between the markings and the specified structures of the eye, it is expedient to provide a coupling between the OCT module and the handpiece. This coupling needs only to be able to realize a rigid connection between the OCT module and the handpiece, without an exact adjustment position in this rigid connection being essential. Through the imaging of the markings using the OCT module, the actual relative position between the OCT scanner and the laser scanner which is present after the production of the rigid connection by means of the coupling is ascertained with high precision. The coupling is preferably fitted without registration structures and brings about an accuracy of the rigid connection in the tenth of a millimetre range, but not more precise.

An example of a coupling is a simple electromagnetic closure which connects the OCT module rigidly to the handpiece. If the rigid connection, which represents a second state of the OCT module and the handpiece, is produced, and if the first relative position which is present in the case of this rigid connection has been ascertained (either before or after the rigid connection is produced), the OCT module can be switched with respect to its axial measurement range without any time requirement. The OCT module then no longer needs to fulfil the requirement to ascertain both the specified structures and the markings simultaneously or essentially at the same time, wherein the term "at the same time" refers to the time scale in which the first relative position or the relative position between the eye and the handpiece could change. If the OCT module has been shifted with respect to its axial measurement range such that it now captures the specified structures, the second relative position, i.e., the relative position between the OCT scanner and the specified structures of the eye, is ascertained. This can, for example, take place when the eye is connected to a contact lens which is provided at the outlet end of the handpiece. From the knowledge of the (now rigidly set) first relative position and from the measurement of the second relative position, the laser scanner can be actuated such that the focus is placed precisely with respect to the specified structures of the eye.

This monitoring of the second relative position can take place continuously, which has the advantage that an attachment of the eye to the contact lens which is as rigid as possible, as has always been sought in the state of the art, is no longer necessary. Rather, a fixing of the eye is also possible now with a certain degree of play, as a variation in the eye position is identified immediately by the OCT capture of the specified structures and the ascertaining of the second relative position, and can be taken into account in the actuation of the laser scanner. A connection of the eye and contact lens which is significantly more rigid vis-à-vis the state of the art is more comfortable for a patient and also has advantages with regard to the implementation of the laser-surgery procedure, as a movement between the eye and the handpiece, which would even lead to the process being terminated in the state of the art, can now be tolerated. It can be identified immediately through the capture of the second relative position on the basis of the imaging of the OCT module and can be compensated for in the actuation of the laser scanner.

In particular for a simple construction of the OCT module to the effect that no large axial measurement range is required, an embodiment of the invention is therefore preferred which, in the method after step b) or c), comprises the fixing of the first relative position by bringing the handpiece and the OCT module into the second state in which the handpiece and the OCT module are rigidly connected. It is analogously provided for the system that the handpiece and/or the OCT module comprises a coupling for the rigid connection of the handpiece to the OCT module. The coupling can be provided exclusively on one of the two parts to be connected, for example, in the form of an electromagnetic closure which can be activated on the handpiece or on the OCT module. Alternatively, the coupling can also be provided on both parts, for example, in the form of a mechanical snap or latch closure, a bayonet mount etc.

The fixing of the eye during the laser-surgery procedure is advantageous. It is therefore to be preferred that a contact lens is applied to the outlet end for attaching the handpiece to the eye. The position of this contact lens does not have any further significance for the adjustment according to the invention, as both the first relative position between the OCT scanner and the laser scanner as well as the second relative position between the OCT scanner and the specified structures of the eye is known through the approach according to the invention. A laborious adjustment of the contact lens with respect to the eye, as is required to some extent in the state of the art, can therefore be dispensed with.

The three markings serve to precisely ascertain the spatial position of the handpiece and thus ultimately of the laser scanner with respect to the OCT scanner. Three point-symmetric markings are sufficient for this.

The markings are arranged on the handpiece. A particularly simple design provides a beam splitter, via which the OCT measurement beam can be coupled into a beam path of the treatment laser beam. In a preferred embodiment, the markings can be applied to this beam splitter, in particular in the form of local variations in the refractive index.

The handpiece contains the laser scanner. In an embodiment, it has a coupling point, e.g., an optical fibre connector for supplying the treatment laser radiation. In an alternative embodiment, the laser beam source is arranged in the handpiece.

The beam splitter can also comprise mirrors, which divert the OCT measurement beam, and also directs further mirror elements attached to the handpiece, in particular in the form of retroreflectors, which guide the OCT measurement beam via the mirrors back to the OCT module. The mirrors on the beam splitter are expediently designed to be as small as possible in order not to disrupt a coupling of the OCT measurement beam into the beam path of the treatment laser beam in the remaining surface of the beam splitter.

Another location for providing the markings is on an optical element, preferably a lens, which precede(s) the exit aperture. Here too, the markings can be provided as local variations in the refractive index, as these can be identified well using the OCT technology.

In order to affect the imaging of the specified structures of the eye using the OCT module as little as possible and at the same time to cause as few interferences for the guiding of the treatment laser beam as possible, it is to be preferred to arrange the markings at the edge or outside of a pupil of the beam path, guiding the treatment radiation, of the handpiece.

The marking elements are generally possible in the form of 3D geometric structures or local variations of the refractive index or a coating structure of an optical element which lies in the beam path on which the OCT measurement beam runs through the handpiece. The markings need not necessarily lie after the coupling of the OCT measurement beam into the beam path of the treatment laser beam.

In an embodiment, the method according to the invention can proceed as follows:

At the start, the laser treatment device with its handpiece is separate from the OCT module, which in particular can be a component of a surgical microscope. The handpiece is now connected, i.e., docked, to the OCT module, in particular the surgical microscope, wherein in a development the docking process can be monitored by means of the OCT module with respect to the alignment of the handpiece and the OCT module (surgical microscope). In any case, before, during or after the docking, the markings are imaged using the OCT module, in order to ascertain the first relative position between the markings and the OCT scanner in the docked state. This phase takes place in the method according to the invention or with the system according to the invention.

In this second state, in which the OCT module and the handpiece are rigidly connected to each other, the handpiece is then applied to the eye. For this, a suitable contact lens is used, which, as is also described below, can also have a fluid contact with the eye, as is described in US 2003/0102895 A1. This step, like the subsequent treatment step in which treatment laser radiation is introduced on the eye, no longer needs to be part of the method for adjusting or of the system, but rather can already be part of a treatment method.

Finally, the connections between the handpiece and the eye and between the OCT module (surgical microscope) and the handpiece are separated again. The contact lens does not need to be firmly connected to the handpiece here. It is also possible that the handpiece is connected to the contact lens in a separate step, for example, after the handpiece and the OCT module have been connected. The same applies to the releasing. The handpiece can be released from the contact lens which is still located on the eye.

It is understood that the features and embodiments named above and those yet to be explained below can be used not only in the stated combinations but also in other combinations or alone, without departing from the scope of the present invention.

BRIEF DESCRIPTION OF THE DRAWINGS

The invention is explained in even more detail below by way of example with reference to the attached drawings, which also disclose features essential to the invention. There are shown in.

DETAILED DESCRIPTION

Figure 1:
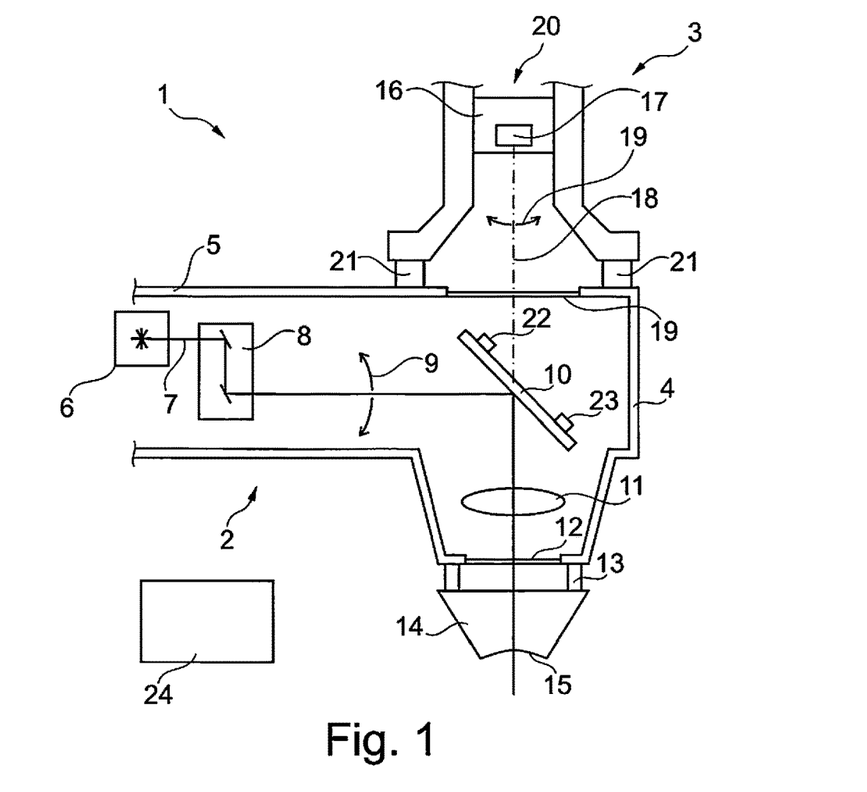
FIG. 1 which is a schematic representation of a system for laser processing comprising an OCT module and a laser treatment device, FIG. 2 which is the spatial arrangement of the OCT module and the laser treatment device of FIG. 1 with respect to an eye to be treated, FIG. 3 which is a representation similar to that of FIG. 2, in a state directly before the start of the treatment, FIGS. 4-7 which are different embodiments of the handpiece of FIG. 1 with respect to the arrangement of the markings, FIG. 8 which is a top view of a lens of the handpiece in the design of FIG. 4, and FIG. 9 depicting different possible forms of the markings used in the handpiece.

Shown schematically in FIG. 1 is a system 1 for laser treatment. The system 1 comprises a laser-based treatment device 2 and an OCT module 3. The laser-based treatment device 2 comprises a handpiece 4, which can be positioned relative to the eye to be treated. The handpiece 4 is arranged in a housing 5, which, in an embodiment, is held via stands etc. such that it can be swivelled and set in three dimensions. The laser-based treatment device 2 comprises a laser 6, which, in an embodiment, lies outside of the housing 5 of the handpiece 4. In another embodiment the laser 6 is arranged in the housing 5.

The laser 6 emits a treatment laser beam 7, which is deflected biaxially from a laser scanner 8. This deflection of the treatment laser beam is illustrated by a double arrow 9. Via a beam splitter 10, the function of which will also be explained later, the treatment laser beam 7 is guided to a lens 11 and from there to an outlet end 5 of the handpiece 4. From the outlet end 12, the treatment laser beam 7 strikes an eye to be treated (not shown in FIG. 1). To fix the eye, in an embodiment a contact lens 14 is provided, which is attached to the outlet end 12 of the handpiece 4 via a releasable attachment device 13, for example, a vacuum attachment. The contact lens 14 has an underside 15, which is put in position against a cornea of the eye to be treated and gives this a known form. The underside 5 is attached to the cornea of the eye preferably by means of vacuum, as is known elsewhere in the state of the art. Embodiments of a contact lens 14 are also known which have a liquid interface with the cornea of the eye. For this, reference is made, by way of example, to US 2013/0102895 A1. Such a contact lens does not deform the cornea of the eye, although a vacuum attachment of the contact lens to the eye then also takes place or can take place.

Figure 2:
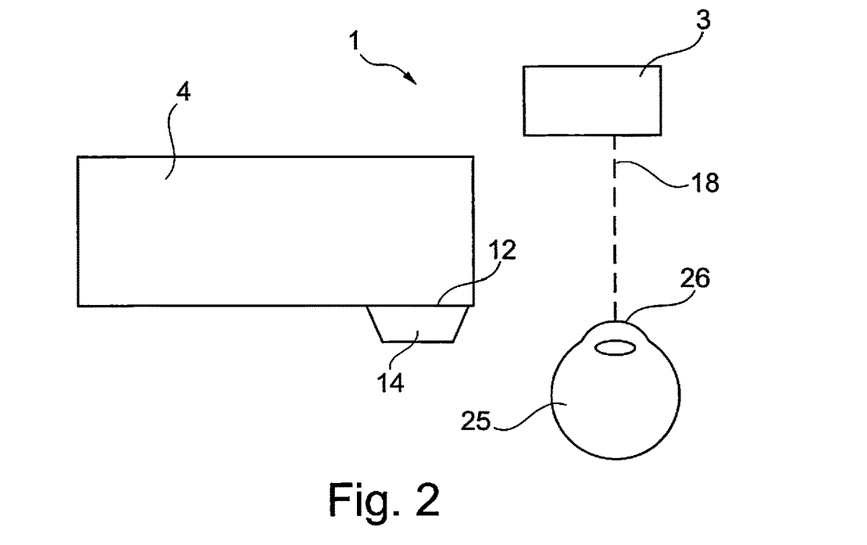

The OCT module 3 is located outside of the housing 5 and is freely movable with respect to the handpiece 4 in a first state. FIG. 2 shows a second state in which the OCT module 3 is rigidly connected to the housing 5 of the handpiece 4 via a coupling, yet to be described. The OCT module 3 has an optical coherence tomograph (OCT) 16, which has an OCT scanner 17, which deflects an OCT measurement beam 18 in two dimensions. The OCT measurement beam 18 is coupled-in via a window 19 in the housing 5 of the handpiece 4. The window 15 represents a coupling point for the OCT measurement beam 18. The OCT measurement beam 18 is incident through the beam splitter 10 and is thus coupled into the beam path of the treatment laser beam 7 and finally strikes the eye. An image of the eye can thus be captured using the OCT 16. In the embodiment represented in FIG. 1, the OCT module is a component of a surgical microscope 20. The OCT module 3 can be rigidly connected to the housing 5 of the handpiece 4 via a coupling 21, which, in the embodiment represented, is designed as an electromagnetic closure on the surgical microscope 20.

The OCT scanner 17 deflects the OCT measurement beam 18 in two dimensions. This is illustrated by an arrow 19. The imaging area realized by means of this in particular captures markings 22, 23, which are arranged on the rear side of the beam splitter 10 (relative to the incidence of the treatment laser beam 7). As the beam splitter 10 is firmly arranged in the housing 5, the markings 22, 23 are also in a fixed position relative to the laser scanner 8. The OCT module 3 can image the markings 22, 23 and thus ascertain the relative position between the OCT scanner 17 and the laser scanner 8. The OCT module 3 can also capture the position of specified structures in the eye, with the result that the second relative position between these specified structures and the OCT scanner 17 is known.

The OCT module 3 and the laser treatment device 2 are actuated by a control device 24 which is optionally also designed in several parts. The control device 24 in particular captures the data provided by the OCT module 3 as image data, ascertains therein the first relative position between the OCT scanner and markings 22, 23, for example, in the form of relative coordinates of the markings 22, 23, again ascertains from the image of the eye the relative position between the OCT scanner 17 and specified structures of the eye and takes into account the first and second relative positions in the actuation of the laser scanner 8.

The laser scanner 8 brings about a three-dimensional shift of the focus of the treatment laser beam 7.

FIG. 2 shows two different stages of the use of the system 1 before the actual laser treatment. These stages are thus carried out without the involvement of a doctor, and can in particular proceed fully automatically under the control of the control device 24.

FIG. 2 shows a first stage, in which an eye 24 is measured using the OCT module 3. The OCT measurement beam 18 strikes the cornea 26 of the eye 25 more or less directly. By "more or less directly" is meant that the OCT measurement beam 18 does not run through the handpiece 4. In the stage of FIG. 1, specified structures of the eye are measured. These structures can in particular comprise the crystalline lens of the eye 5, which is to be removed in a cataract operation and replaced by an implant. In the first stage, the handpiece 4 of the system 1 is not yet placed over the eye 25.

Figure 3:
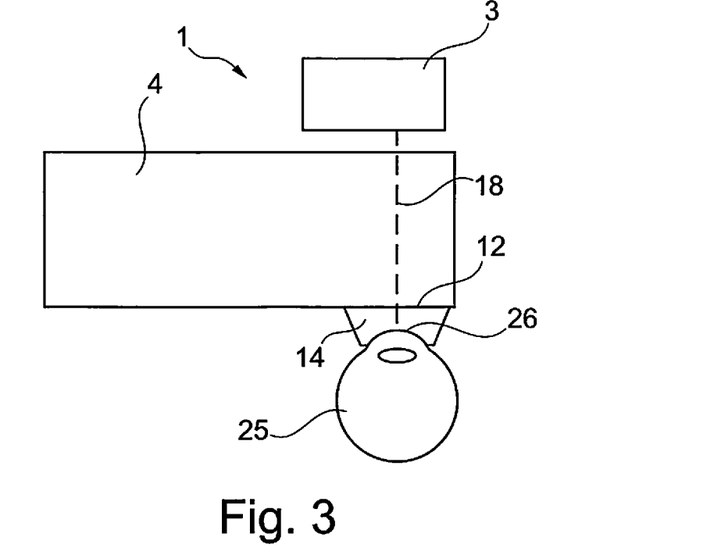

When the measurement of the first stage is finished, the handpiece 4 is placed over the eye 25, for example, in that the contact lens 14 provided on the outlet end 12 is fitted on the cornea 26 of the eye 25. Using its OCT measurement beam 18, the OCT module 3 now captures the specified structures of the eye 25 through the handpiece 4 and in particular through the outlet end 12. At the same time, because of the large depth measurement area of the OCT module 3, the measurement beam 18 can also image the markings 22, 23 in the handpiece 4 (not recorded in FIG. 3). These two imagings take place either simultaneously or so close to each other in time that the time interval between imaging of the specified structures and of the markings is short on the time scale of possible changes in the relative positions.

Figure 4:
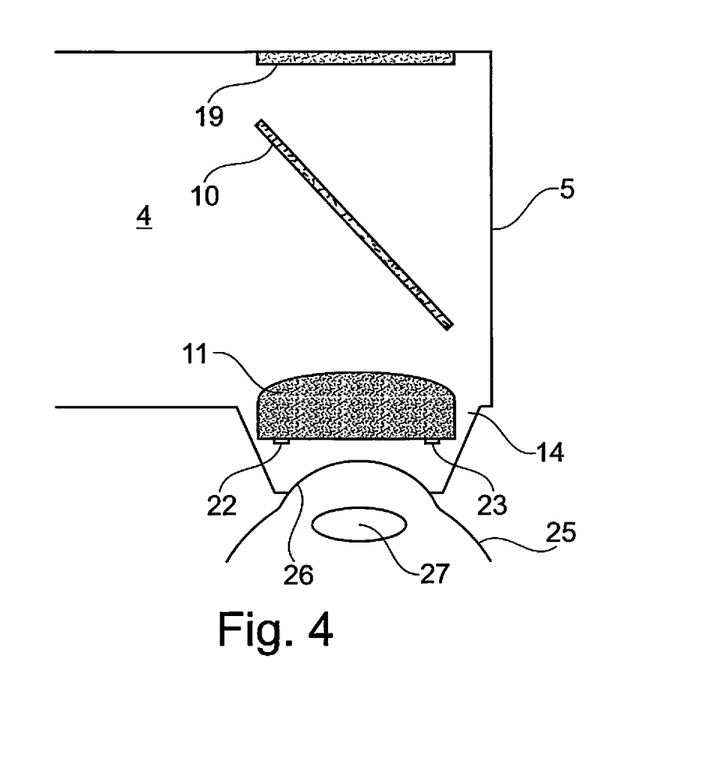

FIG. 4 shows a first embodiment with respect to the arrangement of the markings 22, 23. Here they are arranged on a flat side of the lens 11. Further, the outlet end 12 of the handpiece 4 is the same as the contact lens 14 in FIG. 4 purely by way of example.

Figure 5:
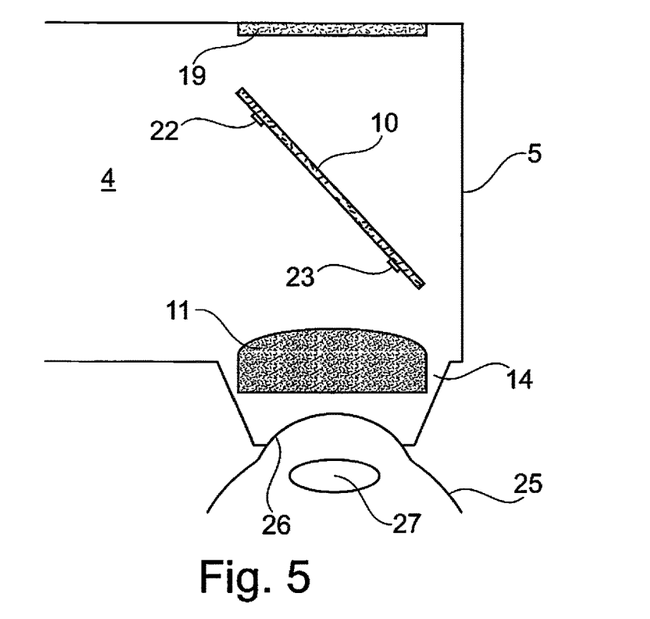

FIG. 5 shows another design, in which the markings 22, 23 lie on the front side (relative to the treatment laser beam 7) of the beam splitter 10.

Figure 6:
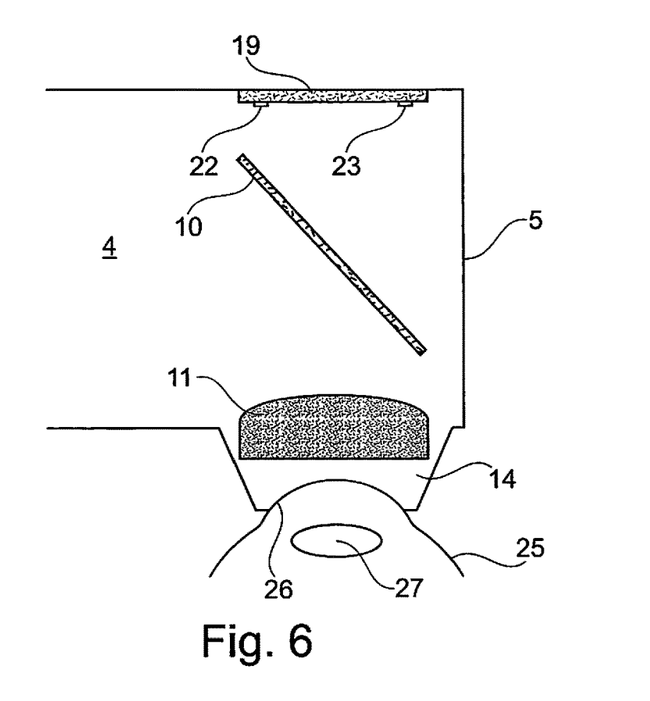

FIG. 6 shows an arrangement of the markings 22, 23 on the inner side of the window 19. In another embodiment they can, of course, also be on the outer side.

Figure 7:
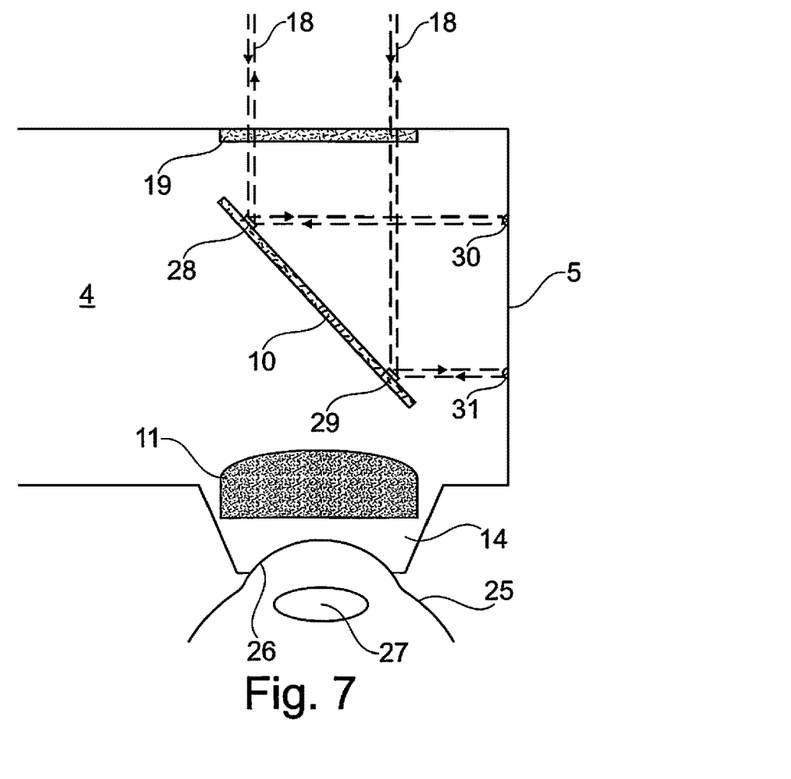

FIG. 7 shows an embodiment in which the markings are formed from mirrors 28, 29 and retroreflectors 30, 31. The mirrors 28, 29 on the rear side of the beam splitter 10 divert the incident OCT measurement beam 18 to the retroreflectors 30, 31, from where they are reflected to the OCT module 3.

Figure 8:
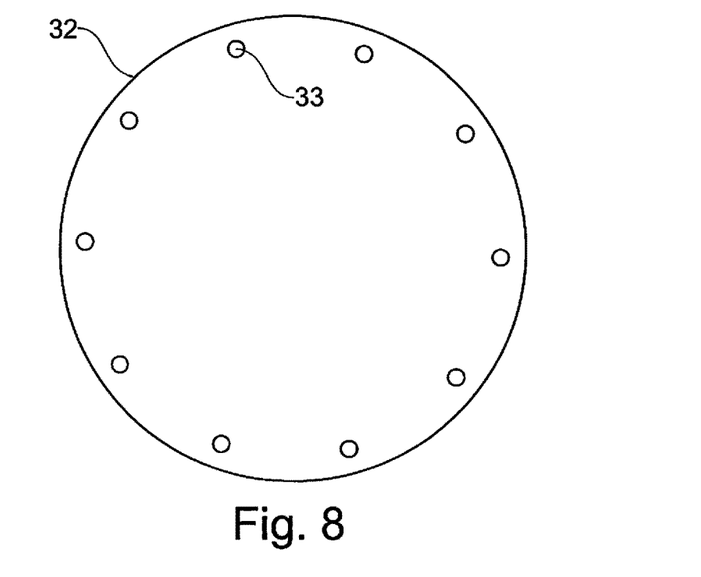

FIG. 8 shows, by way of example, the use of ten markings in the form of points 33 on a surface 32 of an optical element in the beam path between the window 19 and the outlet end 12 of the handpiece 4. This surface can be, for example, the underside of the lens 11 shown in FIG. 4.

Figure 9:
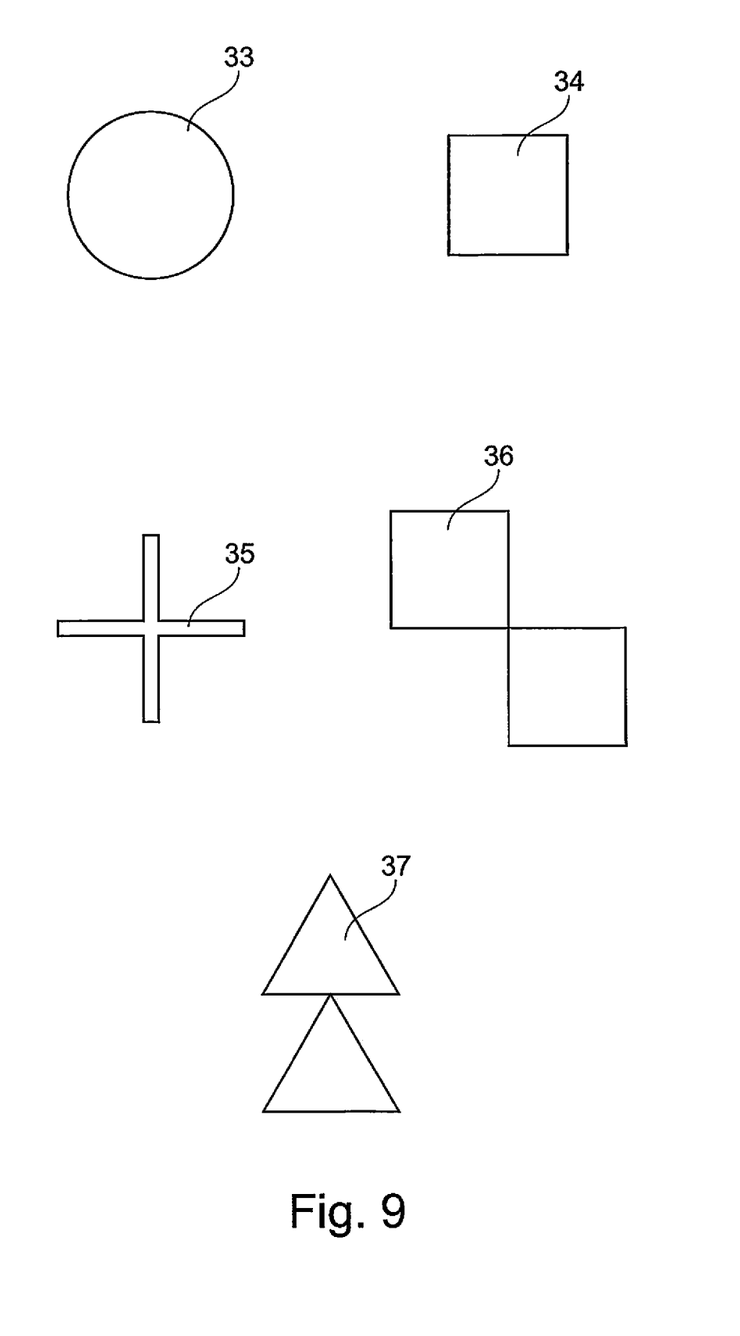

FIG. 9 shows different forms which are possible for the markings. They can be point-symmetric forms, like the forms 33 to 36, or non-point-symmetric structures, like form 37.

The following optional developments and designs come into consideration for embodiments of the system and method for adjustment according to the invention:

The marking is preferably realized within the framework of a coating process of an optical element. The coating can be avoided in a targeted manner at selected locations by masking of the substrate, or be removed subsequently using a sputtering system. For example, the marking can be realized within the framework of an antireflective coating process. At the location of the marking, an increased reflectivity of the substrate for the OCT wavelength is thus hereby achieved.

The marking preferably lies at the edge or outside of the pupil of the beam path of the treatment laser beam.

As the lateral resolution of the OCT image is limited by the numerical aperture of the optical system (and typically lies in the region of 10 µm), markings with a specific form are preferably used (see FIG. 9) in order to improve the measurement accuracy.

For the capture of the position of these markings, edge detection algorithms are preferably used, which can ascertain a geometric primitive (e.g., straight lines, circles, arcs, ellipses) of the marking with subpixel accuracy.

In order to further increase the measurement accuracy, the markings preferably have a point symmetry. As opposite geometric primitives are captured with the same scanning errors, the calculation of the position of the point of symmetry or the central point remains unaffected by this measurement error. In this way, the lateral position of the marking element is ascertained with a measurement uncertainty (MPE—Maximal Permissible Error) which is 5× to 50× smaller than a lateral optical resolution of the OCT module.

In order to achieve a high measurement accuracy along the z-axis (i.e., parallel to the optical main axis of the OCT module), the axial z-extent of the markings is preferably smaller than 1 µm. It is possible, for example, to realize such markings in the framework of the above-described coating method.

Furthermore, several marking elements (preferably 10 or more) are preferably applied to a flat surface of the optical element.

The optical surface preferably has a planarity of less than 1 µm. The accuracy in the measurement of the z-position and of the tilt of the optical element or the scanning unit can thereby be increased on the basis of statistical calculations (e.g., averaging).

The axial measurement range of the OCT module is limited by the scanning area. If the difference of the optical path lengths between the eye and the marking is greater than the axial measurement range of the OCT module 3, a simultaneous measurement of the positions of the eye and of the scanning unit is not possible. The two positions can then be obtained sequentially by a switching of the OCT 16.

In the design of FIG. 7, the OCT measurement beam 18 is diverted in the handpiece and then reflected back using retroreflectors. Through the position of the retroreflectors it is possible to configure the difference in the optical path lengths of the OCT signal from the eye and the reference signal from the retroreflector to be smaller than the measurement range of the OCT module. A simultaneous capture of a position of the markings and of the eye topography and/or of structures in the eye is thereby possible.

The marking elements preferably have a form deviation between 0.01 µm and 10 µm (requirement for accurate edge detection).

The height of the marking elements preferably lies between 0.05 µm and 1 µm.

The surface of the optical element which bears the marking elements preferably has a planarity between 0.05 µm (corresponds to λ/20 at 1,000 nm) and 1 µm (or λ at 1,000 nm).

The invention claimed is:

1. A method for adjusting a scanning laser based treatment device to an eye, wherein the method comprises the following steps:
 a) using a laser-based treatment device which comprises:
  a laser beam source for emitting treatment laser radiation,
  a handpiece into which the treatment laser radiation is coupled in and which comprises an optical marking and an outlet end for emitting the treatment laser radiation into the eye, and
  a controllable laser scanner which is located in the handpiece and arranged between the laser beam source and the outlet end of the handpiece, and is configured to guide the treatment laser radiation over the eye in a scanning manner;
 b) providing an OCT module with a controllable OCT scanner configured for OCT imaging the eye in a scanning manner, wherein the handpiece and the OCT module are freely movable relative to each other in a first state, and the handpiece comprises a OCT module coupling-in point for imaging the eye through the outlet end;
 c1) OCT imaging the optical marking of the handpiece by using the OCT module and the OCT scanner;
 c2) determining a first relative position between the optical marking of the handpiece and the OCT scanner based on the OCT image of the optical marking;
 d) imaging a specified structure of the eye using the OCT module through the handpiece and the outlet end while a relative position between the handpiece, the eye and the OCT module is the same as in step c1), and determining a second relative position between the specified structure of the eye and the OCT scanner based on the image of the specified structure of the eye, the second relative position being different than the first relative position; and
 e) generating signals for controlling the laser scanner on the basis of the first relative position and the second relative position.

2. The method according to claim 1, wherein the handpiece comprises at least three optical markings.

3. The method according to claim 1, wherein the method comprises after step b) or c2) the further following step: fixing of the first relative position by bringing the handpiece and the OCT module into a second state in which the handpiece and the OCT module are rigidly connected.

4. The method according claim 1, further comprising applying a contact lens to the outlet end, wherein the contact lens is configured for attaching the handpiece to the eye.

5. The method according to claim 1, wherein the handpiece comprises a beam splitter, upstream of the exit aperture, which comprises the optical marking, in particular in the form of a local variation in the refractive index.

6. The method according to claim 1, wherein the handpiece comprises a beam splitter upstream of the exit aperture and the optical marking comprises: mirrors on the beam splitter and mirror elements arranged in the handpiece, in particular in the form of retroreflectors.

7. The method according to claim 1, wherein the handpiece comprises a lens, upstream of the exit aperture, which comprises the optical marking, in particular in the form of a local variation in the refractive index.

8. The method according to claim 1, wherein the optical marking lies at an edge or outside of a pupil of a treatment radiation beam path of the handpiece.

9. The method according to claim 1, further comprising determining a relative position between the structure of the eye and the optical marking.

10. The method according to claim 9, wherein generating signals for controlling the laser scanner on the basis of the first relative position and the second relative position includes the generating signals for controlling the laser scanner on the basis of the relative position between the structure of the eye and the optical marking.

* * * * *

UNITED STATES PATENT AND TRADEMARK OFFICE
CERTIFICATE OF CORRECTION

PATENT NO.         : 10,470,930 B2
APPLICATION NO.    : 15/025875
DATED              : November 12, 2019
INVENTOR(S)        : Evangelos Papastathopoulos

Page 1 of 1

It is certified that error appears in the above-identified patent and that said Letters Patent is hereby corrected as shown below:

In the Claims

In Column 11, Line 26, Claim 10 delete "includes the generating" and insert -- includes generating the --, therefore.

Signed and Sealed this
Twenty-first Day of January, 2020

Andrei Iancu
*Director of the United States Patent and Trademark Office*